United States Patent
Krämer et al.

(10) Patent No.: US 9,029,289 B2
(45) Date of Patent: May 12, 2015

(54) CATALYST FOR PREPARING CARBOXYLIC ACIDS AND/OR CARBOXYLIC ANHYDRIDES

(71) Applicant: BASF SE, Ludwigshafen (DE)

(72) Inventors: Michael Krämer, Wadern (DE); Jürgen Zühlke, Speyer (DE); Stefan Altwasser, Stuttgart (DE); Nico Frederik Fischer, Mannheim (DE); Frank Rosowski, Berlin (DE); Hans-Martin Allmann, Neunkirchen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/943,134

(22) Filed: Jul. 16, 2013

(65) Prior Publication Data

US 2014/0018550 A1    Jan. 16, 2014

Related U.S. Application Data

(60) Provisional application No. 61/671,815, filed on Jul. 16, 2012.

(51) Int. Cl.
| | | |
|---|---|---|
| *C07D 307/89* | (2006.01) | |
| *B01J 27/198* | (2006.01) | |
| *B01J 35/00* | (2006.01) | |
| *B01J 23/00* | (2006.01) | |
| *B01J 23/22* | (2006.01) | |
| *B01J 35/10* | (2006.01) | |
| *B01J 37/02* | (2006.01) | |

(52) U.S. Cl.
CPC .............. *B01J 27/198* (2013.01); *C07D 307/89* (2013.01); *B01J 35/0006* (2013.01); *B01J 23/002* (2013.01); *B01J 23/22* (2013.01); *B01J 35/002* (2013.01); *B01J 35/1014* (2013.01); *B01J 37/0221* (2013.01); *B01J 2523/00* (2013.01)

(58) Field of Classification Search
CPC ...... C07D 307/89; B01J 23/22; B01J 27/198; B01J 35/0006; B01J 23/002; B01J 37/0221; B01J 35/1014; B01J 35/002; B01J 2523/00
USPC .............................. 549/248; 562/400; 502/353
See application file for complete search history.

(56) References Cited

U.S. PATENT DOCUMENTS

| | | |
|---|---|---|
| 5,169,820 A | 12/1992 | Ueda et al. |
| 6,362,345 B1 | 3/2002 | Heidemann et al. |
| 6,586,361 B1 | 7/2003 | Heidemann et al. |
| 2007/0060758 A1 | 3/2007 | Storck et al. |
| 2009/0306409 A1 | 12/2009 | Guckel et al. |
| 2010/0210857 A1 | 8/2010 | Storck et al. |
| 2011/0124885 A1 | 5/2011 | Altwasser et al. |
| 2012/0029214 A1 | 2/2012 | Altwasser et al. |

FOREIGN PATENT DOCUMENTS

| | | |
|---|---|---|
| CN | 1054726 A | 9/1991 |
| CN | 1302294 A | 7/2001 |
| DE | 40 06 935 A1 | 9/1991 |
| DE | 19839001 A1 | 3/2000 |
| EP | 522871 A1 | 1/1993 |
| EP | 1636161 A1 | 3/2006 |
| WO | WO-2004103561 A1 | 12/2004 |
| WO | WO-2011061132 A1 | 5/2011 |
| WO | WO-2012014154 A1 | 2/2012 |

OTHER PUBLICATIONS

Golunski, S. E., et al., "Antimony Oxides: a Guide to Phase Changes During Catalyst Preparation", Applied Catalysis, 1989, vol. 48, pp. 123-135.

Hansen, S., et al., "The Crystal Structure of $Sb_{0.92}V_{0.92}O_4$, Determinde by Neutron and Dual Wavelength X-Ray Powder Diffraction", Journal of Solid State Chemistry, 1993, vol. 102, pp. 340-348.

Schubert, U.-A., et al., "Possible Effects of Site Isolation in Antimony Oxide-Modified Vanadia/Titania Catalysts for Selective Oxidation of o-Xylene", Topics in Catalysis, 2001, vol. 15, No. 2-4, pp. 195-200.

Sunandana, C. S., et al., "ESR Evidence for the Existence of Rutile-Type, Nonstoichiometric Vanadium Antimonate", Mat. Res. Bull., 1984, vol. 19, pp. 325-329.

Vernon, L. W., et al., "The Crystal Structure of Rutile-Like Heavy Metal Orthovanadates", The Texas Journal of Science, 1951, No. 1, pp. 82-85.

International Search Report for PCT/IB2013/055729, mailing date Jan. 2, 2014.

*Primary Examiner* — T. Victor Oh

(74) *Attorney, Agent, or Firm* — Drinker Biddle & Reath LLP

(57) ABSTRACT

The present invention relates to a catalyst for preparing carboxylic acids and/or carboxylic anhydrides, which has a plurality of catalyst zones arranged in series and has been produced using a vanadium antimonate having a maximum content of crystalline valentinite of 5% by weight. The present invention further relates to a process for gas-phase oxidation in which a gas stream comprising at least one hydrocarbon and molecular oxygen is passed through a catalyst which has a plurality of catalyst zones arranged in series and has been produced using a vanadium antimonate having a maximum content of crystalline valentinite of 5% by weight.

5 Claims, No Drawings

CATALYST FOR PREPARING CARBOXYLIC ACIDS AND/OR CARBOXYLIC ANHYDRIDES

CROSS-REFERENCE TO RELATED APPLICATIONS

This application claims benefit (under 35 USC 119(e)) of U.S. Provisional Application 61/671,815, filed Jul. 16, 2012, which is incorporated by reference.

The present invention relates to a catalyst for preparing carboxylic acids and/or carboxylic anhydrides, which has a plurality of catalyst zones arranged in series and has been produced using a vanadium antimonate having a maximum content of crystalline valentinite of 5% by weight. The present invention further relates to a process for gas-phase oxidation in which a gas stream comprising at least one hydrocarbon and molecular oxygen is passed through a catalyst which has a plurality of catalyst zones arranged in series and has been produced using a vanadium antimonate having a maximum content of crystalline valentinite of 5% by weight.

Many carboxylic acids and/or carboxylic anhydrides are prepared industrially by the catalytic gas-phase oxidation of hydrocarbons such as benzene, the xylenes, naphthalene, toluene or durene in fixed-bed reactors. In this way, it is possible to obtain, for example, benzoic acid, maleic anhydride, phthalic anhydride (PAn), isophthalic acid, terephthalic acid or pyromellitic anhydride. In general, a mixture of an oxygen-comprising gas and the starting material to be oxidized is passed through tubes in which a bed of a catalyst is present. To regulate the temperature, the tubes are surrounded by a heat transfer medium, for example a salt melt.

Coated catalysts in which the catalytically active composition has been applied in the form of a shell to an inert support material such as steatite have been found to be useful as catalysts for these oxidation reactions. In general, the catalysts have an active composition layer having an essentially homogeneous chemical composition which is applied in the form of a shell. Furthermore, two or more different active composition layers can also be applied in succession to a support. This is then referred to as a two-layer or multilayer catalyst (see, for example, DE 19839001 A1).

Titanium dioxide and vanadium pentoxide are generally used as catalytically active constituents of the catalytically active composition of these coated catalysts. Furthermore, small amounts of many other oxidic compounds which act as promoters to influence the activity and selectivity of the catalyst, including cesium, phosphorus and antimony oxides, can be comprised in the catalytically active composition.

The presence of antimony oxides leads to an increase in the PAn selectivity, an effect which is considered to be due to individualization of the vanadium sites. The antimony oxides used in the active composition of the catalysts can be various antimony(III), antimony(IV) or antimony(V) compounds; it is usual to use antimony trioxide or antimony pentoxide. EP 522871 describes the use of antimony pentoxide, US 2009/306409 and EP 1636161 disclose the use of antimony trioxide. Catalysts giving a particularly high PAn yield can, according to EP 1636161, be obtained when particular $V_2O_5$/$Sb_2O_3$ ratios are set and the antimony trioxide has a defined average particle size.

Compared to antimony tetroxide and antimony pentoxide, antimony trioxide is better able to spread on titanium dioxide, achieving a significantly better distribution on the catalyst. There are two different modifications of antimony trioxide, viz. the cubic senarmontite and the orthorhombic valentinite (Golunski, S. E. et al., Appl. Catal., 1989, Vol. 48, pages 123 to 135). Phase-pure senarmontite is typically used as antimony trioxide (cf. Schubert, U.-A. et al., Topics in Catalysis, 2001, Vol. 15(2-4), pages 195 to 200). WO 2012/014154 describes an increase in the PAn yield when an antimony trioxide having a valentinite content of at least 2% is used.

To produce such catalysts, it is possible to use not only the pure oxides of antimony and of vanadium but also a vanadium antimonate which can be obtained by reaction of suitable vanadium and antimony compounds, for example the oxides (WO 2011/61132). The use of such a vanadium antimonate in at least one zone of a PAn catalyst leads to comparatively low hot spot temperatures (<425° C.) at o-xylene loadings in the range from 80 to 100 g/standard $m^3$. The PAn yields are higher than those given by comparable catalysts without crystalline vanadium antimonate.

In chemical reactions of two crystalline phases to form another mixed phase, for example the reaction of vanadium oxide with antimony oxide to form crystalline vanadium antimonate, incomplete reactions of the individual starting materials frequently occur. The resulting product is in such cases not phase-pure but instead comprises one or more further phases.

There is a continual need for catalysts for gas-phase oxidations which give a very high conversion with high selectivity.

It was an object of the present invention to develop a catalyst for preparing carboxylic acids and/or carboxylic anhydrides, in particular for the oxidation of o-xylene and/or naphthalene to phthalic anhydride, which makes high yields at a low content of by-products possible at low salt bath temperatures.

This object is achieved by a catalyst for preparing carboxylic acids and/or carboxylic anhydrides, which has a plurality of catalyst zones arranged in series and in the production of which a vanadium antimonate having a maximum content of crystalline valentinite of 5% by weight is added to at least one zone.

For the purposes of the present invention, a vanadium antimonate is a substance which comprises a crystalline vanadium antimonate phase (for example Powder Diffraction File (PDF) No.: 01-81-1219, PDF: 01-77-0331 or PDF: 37-1075) as substantial component. Apart from further amorphous materials, the vanadium antimonate phase can also comprise small amounts of other crystalline components, in particular pure oxides of vanadium and/or of antimony.

The quantitative determination of the proportion of crystalline valentinite in the vanadium antimonate phase can, for example, be carried out by means of Rietveld refining of X-ray powder diffraction patterns.

The vanadium antimonate having a maximum content of crystalline valentinite of 5% by weight which is to be used according to the invention can be used for producing one or more catalyst zones. In a preferred embodiment of the invention, the catalyst has three, four or five zones, with vanadium antimonate having a maximum content of crystalline valentinite of 5% by weight having been used for producing at least one zone.

The catalysts of the invention have a plurality of catalyst zones which are arranged in series and can differ in terms of their content of catalytically active composition and chemical make-up and also in terms of their catalytic activity. In general, catalysts in which the activity of the individual catalyst zones increases from the reactor inlet to the reactor outlet are preferred. However, it is also possible to use one or more preceding or intermediate catalyst zones which have an activity higher than that of the subsequent zones.

The catalysts of the invention can, for example, be used to avoid high hot spot temperatures, including in combination with suitable upstream and/or downstream beds and also together with intermediate zones, with the upstream and/or downstream beds and also the intermediate zones generally being able to comprise catalytically inactive or less active material.

The catalysts according to the invention are generally coated catalysts in which the catalytically active composition has been applied in the form of a shell to an inert support material.

As inert support material, it is possible to use virtually all support materials of the prior art as are advantageously used in the production of coated catalysts for the oxidation of aromatic hydrocarbons to aldehydes, carboxylic acids and/or carboxylic anhydrides, for example quartz ($SiO_2$), porcelain, magnesium oxide, tin dioxide, silicon carbide, rutile, alumina ($Al_2O_3$), aluminum silicate, steatite (magnesium silicate), zirconium silicate, cesium silicate or mixtures of these support materials. The catalyst supports can, for example, be used in the form of spheres, rings, pellets, spirals, tubes, extrudates or crushed material. The dimensions of these catalyst supports correspond to those of catalyst supports customarily used for producing coated catalysts for gas-phase reactions of aromatic hydrocarbons. Preference is given to using steatite in the form of spheres having a diameter of from 3 to 6 mm or rings having an external diameter of from 5 to 9 mm and a length of from 3 to 8 mm and a wall thickness of from 1 to 2 mm.

The catalysts of the invention comprise a catalytically active composition which comprises at least vanadium oxide or vanadium antimonate and titanium dioxide and can be applied in one or more layers to the support material. Various layers can differ in terms of their chemical make-up.

The catalytically active composition preferably comprises, based on the total amount of the catalytically active composition, from 1 to 40% by weight of a vanadium compound, calculated as $V_2O_5$, and 60 to 99% by weight of titanium dioxide, calculated as $TiO_2$. In preferred embodiments, the catalytically active composition can additionally comprise up to 1% by weight of a cesium compound, calculated as Cs, up to 1% by weight of a phosphorus compound, calculated as P, and up to 10% by weight of an antimony compound, calculated as $Sb_2O_3$. All figures relating to the chemical make-up of the catalytically active composition are based on the calcined state of the latter, e.g. after calcination of the catalyst for one hour at 450° C.

Titanium dioxide is usually used in the anatase form for the catalytically active composition. The titanium dioxide preferably has a BET surface area of from 15 to 60 $m^2/g$, in particular from 15 to 45 $m^2/g$, particularly preferably from 13 to 28 $m^2/g$. The titanium dioxide used can consist of a single titanium dioxide or a mixture of titanium dioxides. In the latter case, the value of the BET surface area is the weighted average of the contributions of the individual titanium dioxides. The titanium dioxide used advantageously comprises, for example, a mixture of a $TiO_2$ having a BET surface area of from 5 to 15 $m^2/g$ and a $TiO_2$ having a BET surface area of from 15 to 50 $m^2/g$. Particularly suitable vanadium sources are vanadium pentoxide, ammonium metavanadate and vanadium antimonate. Suitable antimony sources are various antimony trioxides and vanadium antimonate. Possible ways of limiting the content of crystalline valentinite in the crystalline vanadium antimonate to a maximum of 5% by weight are diverse and known to those skilled in the art. One possibility is, for example, the use of a low-valentinite or valentinite-free antimony oxide as antimony source. Products such as Selectipur 7835 (from Merck), Triox White (from Antraco), ACC-BS (from Antraco) or Zero valentinite (from Campine) are commercially available. In addition, the content of crystalline valentinite can be controlled by means of the reaction conditions during the reaction of the vanadium and antimony compounds, preferably the respective oxides. Parameters such as particle size of the starting materials used, reaction time, reaction temperature and thermal after-treatment and molar V/Sb ratio play a role here.

As phosphorus source, it is possible to use, in particular, phosphoric acid, phosphorous acid, hypophosphorous acid, ammonium phosphate or phosphoric esters and especially ammonium dihydrogenphosphate. As sources of cesium, it is possible to use the oxide or hydroxide or salts which can be converted thermally into the oxide, for example carboxylates, in particular the acetate, malonate or oxalate, carbonate, hydrogen carbonate, sulfate or nitrate.

Apart from the optional additions of cesium and phosphorus, many other oxidic compounds which act as promoters to influence the activity and selectivity of the catalyst, for example by reducing or increasing its activity, can be comprised in small amounts in the catalytically active composition. As such promoters, mention may be made by way of example of the alkali metals, in particular, apart from the abovementioned cesium, lithium, potassium and rubidium, which are usually used in the form of their oxides or hydroxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony tetroxide, antimony pentoxide and cerium oxide.

Among the promoters mentioned, further preference is given to the oxides of niobium and tungsten in amounts of from 0.01 to 0.50% by weight, based on the catalytically active composition, as additives.

The application of the layer(s) of the coated catalyst is advantageously carried out by spraying a suspension of $TiO_2$ and $V_2O_5$, which optionally contains sources of the abovementioned promoter elements, onto the fluidized support. Before the coating operation, the suspension is preferably stirred for sufficiently long, e.g. from 2 to 30 hours, in particular from 12 to 25 hours, to break up agglomerates of the suspended solids and give a homogeneous suspension. The suspension typically has a solids content of from 20 to 50% by weight. The suspension medium is generally aqueous, e.g. water itself or an aqueous mixture with a water-miscible organic solvent such as methanol, ethanol, isopropanol, formamide and the like.

In general, organic binders, preferably copolymers, advantageously in the form of an aqueous dispersion, of acrylic acid-maleic acid, vinyl acetate-vinyl laurate, vinyl acetate-acrylate, styrene-acrylate and vinyl acetate-ethylene, are added to the suspension. The binders are commercially available as aqueous dispersions having a solids content of, for example, from 35 to 65% by weight. The amount of such binder dispersions which is used is generally from 2 to 45% by weight, preferably from 5 to 35% by weight, particularly preferably from 7 to 20% by weight, based on the weight of the suspension.

The support is fluidized in an ascending stream of gas, in particular air, in, for example, a fluidized-bed apparatus. The apparatuses usually comprise a conical or spherical vessel into which the fluidizing gas is introduced from below or from above via an immersed tube. The suspension is sprayed in via nozzles from above, from the side or from below into the fluidized bed. The use of a riser tube arranged centrally or concentrically around the immersion tube is advantageous. A higher gas velocity prevails in the riser tube and transports the support particles upward. In the outer ring, the gas velocity is only slightly above the loosening velocity. The particles are thus conveyed vertically in a circular motion. A suitable fluidized-bed apparatus is described, for example, in DE-A 4006935.

Coating temperatures of from 20 to 500° C. are generally employed in the coating of the catalyst support with the catalytically active composition, and coating can be carried out under atmospheric pressure or under reduced pressure. In general, coating is carried out at from 0° C. to 200° C., preferably from 20 to 150° C., in particular from 60 to 120° C.

The layer thickness of the catalytically active composition is generally from 0.02 to 0.2 mm, preferably from 0.05 to 0.15 mm. The proportion of active composition in the catalyst is usually from 5 to 25% by weight, mostly from 7 to 15% by weight.

As a result of the thermal treatment at temperatures of from >200 to 500° C. of the precatalyst obtained in this way, the binder is given off from the applied layer by thermal decomposition and/or combustion. The thermal treatment is preferably carried out in situ in the gas-phase oxidation reactor.

The invention further provides a process for producing a catalyst for the preparation of carboxylic acids and/or carboxylic anhydrides, which has a plurality of catalyst zones arranged in series, wherein a vanadium antimonate having a maximum content of crystalline valentinite of 5% by weight is added to at least one zone.

The invention further provides a process for gas-phase oxidation, in which a gas stream comprising at least one hydrocarbon and molecular oxygen is passed through a catalyst which has a plurality of catalyst zones arranged in series and in the production of which a vanadium antimonate having a maximum content of crystalline valentinite of 5% by weight was added to at least one zone.

The process of the invention is advantageously suitable for the gas-phase oxidation of aromatic $C_6$-$C_{10}$-hydrocarbons such as benzene, the xylenes, toluene, naphthalene or durene (1,2,4,5-tetramethylbenzene) to carboxylic acids and/or carboxylic anhydrides such as maleic anhydride, phthalic anhydride, benzoic acid and/or pyromellitic dianhydride. The process is particularly suitable for preparing phthalic anhydride from o-xylene and/or naphthalene. The gas-phase reactions for preparing phthalic anhydride are generally known and are described, for example, in WO 2004/103561 on page 6.

A preferred embodiment of the invention is a process for the gas-phase oxidation of o-xylene and/or naphthalene to phthalic anhydride, in which a gas stream comprising o-xylene and/or naphthalene and molecular oxygen is passed through a catalyst which has a plurality of catalyst zones arranged in series and in the production of which a vanadium antimonate having a maximum content of crystalline valentinite of 5% by weight was added to at least one zone.

The invention further provides for the use of a catalyst which has a plurality of catalyst zones arranged in series and in the production of which a vanadium antimonate having a maximum content of crystalline valentinite of 5% by weight was added to at least one zone for preparing carboxylic acids and/or carboxylic anhydrides.

EXAMPLES

X-Ray-Crystallographic Determination of the Valetinite Content and the Senarmontite Content in the Antimony Trioxide and in the Vanadium Antimonate The determination was carried out by means of X-ray powder diffractometry. For this purpose, the pulverulent samples were measured in a "D8 Bruker AXS Theta/Theta" X-ray powder diffractometer. The measurement parameters were as follows:

| | |
|---|---|
| Circle diameter | 500 mm |
| X-radiation | CuK-alpha ($\lambda = 1.54 \cdot 10^{-10}$ m) |
| Tube voltage | 40 kV |
| Tube current | 40 mA |
| Aperture | variable V20 |
| Antiscatter orifice | variable V20 |
| Sol-X detector | |
| Step width | 0.02° 2Θ |
| Step mode | continuous |
| Measurement time | 3.6 s/step |

The quantitative determination of the crystalline materials (valentinite, senarmontite and the vanadium antimonate phase) was carried out by means of Rietveld refining (Topas, Bruker AXS).

Catalyst Synthesis:

Catalyst Zone CZ1:

(Vanadium antimonate having a valentinite content of about 3% as V and Sb source, according to the invention):

Preparation of the Vanadium Antimonate:

1223.6 g of vanadium pentoxide and 783.2 g of antimony trioxide (Merck Selectipur 7835, 16% valentinite and 84% senarmontite; $Sb_2O_3 \geq 99.8\%$ by weight; As 200 ppm by weight, Pb 200 ppm by weight, Fe≤100 ppm by weight of Fe, average particle size=2 μm) were suspended in 3.0 l of demineralized water and the suspension was stirred under reflux for 16 hours. The suspension was subsequently stirred at 25° C. for 24 hours before being dried at 100° C. for 10 hours in a vacuum drying oven. Subsequent grinding in a mortar gave a powder having a BET surface area of 64 m²/g and a vanadium content of 32% by weight and an antimony content of 30% by weight. The product had the following crystalline constituents: valentinite (PDF 11-0689): about 3%; vanadium antimonate (PDF: 01-81-1219): about 97%. The average crystallite size of the vanadium antimonate was about 12 nm.

Suspension Batch and Coating:

2 kg of steatite rings (magnesium silicate) having dimensions of 7 mm×7 mm×4 mm were coated in a fluidized-bed apparatus with 768 g of a suspension composed of 4.44 g of cesium carbonate, 413.7 g of titanium dioxide (Fuji TA 100 CT; anatase, BET surface area 27 m²/g), 222.1 g of titanium dioxide (Fuji TA 100; anatase, BET surface area 7 m²/g), 91.6 g of the vanadium antimonate prepared as described above, 1869 g of demineralized water and 78.4 g of organic binder (copolymer of vinyl acetate and vinyl laurate in the form of a 50% strength by weight aqueous dispersion).

After calcination of the catalyst for one hour at 450° C., the amount of active composition applied to the steatite rings was 8.4% by weight. Analysis of the active composition gave contents of 7.1% of $V_2O_5$, 4.5% of $Sb_2O_3$, 0.50% of Cs, balance $TiO_2$.

Catalyst Zone CZ2:

(Vanadium antimonate having a valentinite content of about 7% as V and Sb source; not according to the invention):

Preparation of the Vanadium Antimonate:

2855.1 g of vanadium pentoxide and 1827.5 g of antimony trioxide (Merck Selectipur 7835, 16% valentinite and 84% senarmontite; $Sb_2O_3 \geq 99.8\%$ by weight; As 200 ppm by weight, Pb 200 ppm by weight, Fe≤100 ppm by weight of Fe, average particle size=2 μm) were suspended in 7.0 l of demineralized water and the suspension was stirred under reflux for 16 hours. The suspension was subsequently cooled to 90°

C. and dried by means of spray drying. The inlet temperature was 340° C., the outlet temperature was 110° C. The spray-dried powder obtained in this way had a BET surface area of 65 m$^2$/g and had a vanadium content of 32% by weight and an antimony content of 30% by weight. The product had the following crystalline constituents: valentinite (PDF: 11-0689): about 7%; senarmontite (PDF: 43-1071): about 1%; vanadium antimonate (PDF: 01-81-1219): about 92%. The average crystallite size of the vanadium antimonate was about 9 nm.

Suspension Batch and Coating:

Production analogous to CZ1, with the vanadium antimonate described in CZ2 being used for production.

After calcination of the catalyst for one hour at 450° C., the amount of active composition applied to the steatite rings was 8.3% by weight. Analysis of the active composition gave contents of 7.1% of $V_2O_5$, 4.5% of $Sb_2O_3$, 0.50% of Cs, balance $TiO_2$.

In contrast to CZ1 and CZ2, vanadium pentoxide and antimony trioxide were used instead of vanadium antimonate as V and Sb source in CZ3, CZ4, CZ5 and CZ6. Instead of $TiO_2$ of the Fuji TA 100 CT type, $TiO_2$ of the Fuji TA 100 C type (BET surface area: 20 m$^2$/g) was used in CZ3, CZ4 and CZ5.

Catalyst Zone CZ3:

(Vanadium Pentoxide and Antimony Trioxide as V and Sb Source)

Production analogous to CZ1 with variation of the chemical make-up of the suspension. After calcination of the catalyst for one hour at 450° C., the amount of active composition applied to the steatite rings was 9.1% by weight. Analysis of the active composition gave contents of 7.1% of $V_2O_5$, 1.8% of $Sb_2O_3$, 0.38% of Cs, balance $TiO_2$.

Catalyst Zone CZ4:

(Vanadium Pentoxide and Antimony Trioxide as V and Sb Source)

Production analogous to CZ1 with variation of the chemical make-up of the suspension. After calcination of the catalyst for one hour at 450° C., the amount of active composition applied to the steatite rings was 8.5% by weight. Analysis of the active composition gave contents of 7.95% of $V_2O_5$, 2.7% of $Sb_2O_3$, 0.31% of Cs, balance $TiO_2$.

Catalyst Zone CZ5:

Production analogous to CZ1 with variation of the chemical make-up of the suspension. After calcination of the catalyst for one hour at 450° C., the amount of active composition applied to the steatite rings was 8.5% by weight. Analysis of the active composition gave contents of 7.1% of $V_2O_5$, 2.4% of $Sb_2O_3$, 0.10% of Cs, balance $TiO_2$.

Catalyst Zone CZ6:

Production analogous to CZ1 with variation of the chemical make-up of the suspension. After calcination of the catalyst for one hour at 450° C., the amount of active composition applied to the steatite rings was 9.1%. Analysis of the active composition gave contents of 20% of $V_2O_5$, 0.38% of P, balance $TiO_2$.

Catalytic Oxidation of O-Xylene to Phthalic Anhydride on a Model Tube Scale

Example 1

According to the Invention

The catalytic oxidation of o-xylene to phthalic anhydride was carried out in a salt bath-cooled tube reactor having an internal tube diameter of 25 mm. From the reactor inlet to the reactor outlet, 80 cm of CZ1, 60 cm of CZ3, 70 cm of CZ4, 50 cm of CZ5 and 60 cm of CZ6 were introduced into a 3.5 m long iron tube having an internal diameter of 25 mm. The iron tube was surrounded by a salt melt to regulate the temperature, and a temperature sensor housing having an external diameter of 4 mm and a built-in withdrawable element served to measure the catalyst temperature.

4.0 standard m$^3$/h of air having a loading of 99.2% strength by weight o-xylene of 80 g/standard m$^3$ were passed through the tube from reactor inlet to reactor outlet. This gave the results summarized in Table 1 ("PAn yield" is the phthalic anhydride obtained in percent by weight, based on 100%-pure o-xylene).

Example 2

Oxidation of O-Xylene to Phthalic Anhydride on a Model Tube Scale, not According to the Invention See example 1, but using a catalyst bed from reactor inlet to reactor outlet made up of 80 cm of CZ2, 60 cm of CZ3, 70 cm of CZ4, 50 cm of CZ5 and 60 cm of CZ6.

TABLE 1

| Model tube results | Example 1 (according to the invention) | Example 2 (not according to the invention) |
|---|---|---|
| Amount of air [standard m$^3$/h] | 4.0 | 4.0 |
| Loading [g/standard m$^3$] | 80 | 80 |
| Time of operation [days] | 29 | 35 |
| Salt bath temperature [° C.] | 349 | 351 |
| PAn yield [% by weight] | 114.7 | 113.9 |
| o-Xylene content [% by weight] | 0.05 | 0.05 |
| Phthalide content [% by weight] | 0.09 | 0.12 |
| Hot spot temperature [° C.] | 421 | 420 |

The hot spot temperatures were in both cases below 425° C.

The PAn yield in example 1 is significantly higher than in example 2. The phthalide content is lower in example 1 than in example 2.

The invention claimed is:

1. A catalyst for preparing carboxylic acids and/or carboxylic anhydrides, which has a plurality of catalyst zones arranged in series and in the production of which a vanadium antimonate having a maximum content of crystalline valentinite of 5% by weight is added to at least one zone.

2. A process for producing a catalyst for the preparation of carboxylic acids and/or carboxylic anhydrides, which has a plurality of catalyst zones arranged in series, wherein a vanadium antimonate having a maximum content of crystalline valentinite of 5% by weight is added to at least one zone.

3. A process for gas-phase oxidation which comprises passing a gas stream comprising at least one hydrocarbon and molecular oxygen through the catalyst as claimed in claim 1.

4. A process for the gas-phase oxidation of o-xylene and/or naphthalene to phthalic anhydride which comprises passing a gas stream comprising o-xylene and/or naphthalene and molecular oxygen through the catalyst as claimed in claim 1.

5. A process for preparing carboxylic acids and/or carboxylic anhydrides which comprises utilizing the catalyst according to claim 1.

* * * * *